US006399637B1

(12) United States Patent
Filić et al.

(10) Patent No.: US 6,399,637 B1
(45) Date of Patent: Jun. 4, 2002

(54) CRYSTAL MODIFICATION OF TORASEMIDE

(75) Inventors: Darko Filić; Miljenko Dumić, both of Zagreb; Aleksandar Danilovski, Rijeka; Božena Klepić, Jastrebarsko; Ines Fistrić, Zagreb; Marina Orešić, Sesvete; Jasna Horvat Mikulčić, Zagreb, all of (HR)

(73) Assignee: PLIVA, farmaceutska, kemijska, prehrambena i kozmeticka industrija, dionicko drustvo, Zagreb (HR)

(*) Notice: Subject to any disclaimer, the term of this patent is extended or adjusted under 35 U.S.C. 154(b) by 0 days.

(21) Appl. No.: 09/434,439

(22) Filed: Nov. 5, 1999

Related U.S. Application Data

(63) Continuation of application No. 09/187,046, filed on Nov. 6, 1998, now abandoned.

(30) Foreign Application Priority Data

Feb. 10, 1998 (HR) .......................................... P980532A

(51) Int. Cl.[7] ...................... A61K 31/47; C07D 213/62; C07D 213/71
(52) U.S. Cl. .......................................... 514/347; 546/294
(58) Field of Search ............................ 546/294; 514/347

(56) References Cited

U.S. PATENT DOCUMENTS

| | | | | |
|---|---|---|---|---|
| 4,018,929 A | * | 4/1977 | Delarge et al. ............. | 514/347 |
| 4,055,650 A | * | 10/1977 | DeLarge et al. ............. | 514/347 |
| RE30,633 E | * | 6/1981 | DeLarge et al. ............. | 514/347 |
| RE34,580 E | * | 4/1994 | Topfmeier et al. ........... | 546/291 |
| RE34,672 E | * | 7/1994 | Topfmeier et al. ........... | 514/347 |
| 5,914,336 A | * | 6/1999 | Dreckmann-Behrendt .. | 514/347 |
| 6,166,045 A | * | 12/2000 | Dreckmann-Behrendt et al. ............................................ | 514/347 |

FOREIGN PATENT DOCUMENTS

EP 0212537 * 8/1986 ................. 514/347

OTHER PUBLICATIONS

P.L. Dupont, et al. Structure Cristalline et Moléculaire d'un Diurétique Dérivé de 1'Alkyl–1 [(Phénylamino–4 pyridyl–3)sulfonyl]–3 Urée: la Torasémide ($C_{15}H_{20}N_4SO_3$) Acta Cyrst. B34:1304–1310 (1978).

Rollinger, J. M. et al., Crystal forms torasemide: new insights, *European Journal of Pharmaceutics and Biopharmaceutics*, 53 (2002) 75–86 (Aug. 17, 2001).

* cited by examiner

*Primary Examiner*—Alan L. Rotman
(74) *Attorney, Agent, or Firm*—Finnegan, Henderson, Farabow, Garrett & Dunner, L.L.P.

(57) ABSTRACT

The present invention relates to the characterization of a new crystal modification III of torasemide, to a process for the preparation thereof by the use of controlled acidifying of alkaline solutions of torasemide with inorganic or organic acids with or without addition of a crystal seed, to its use a raw material for the preparation of the crystal modification I of torasemide and of pharmaceutically acceptable salts of torasemide as well as to pharmaceutical forms containing this new crystal modification III of torasemide.

24 Claims, 1 Drawing Sheet

CRYSTAL MODIFICATION OF TORASEMIDE

CROSS-REFERENCE

This application is a continuation of Ser. No. 09/187,046, filed Nov. 6, 1998, abandoned.

TECHNICAL FIELD

The present invention relates to a new crystal modification of N-(1-methylethyl aminocarbonyl)-4-(3-methylphenylamino)-3-pyridinesulfonamide (in the further text of the application designated by its generic name "torasemide"), particularly to a new crystal modification III of torasemide, to processes for its preparation, to its use as a raw material for the preparation of the crystal modification I of torasemide and of pharmaceutically acceptable salts of torasemide as well as to pharmaceutical forms containing the said new modification III of torasemide as the active ingredient.

BACKGROUND OF INVENTION

Torasemide is a compound with interesting pharmacological properties, which is described in DE patent 25 16 025 (Example 71). As a diuretic of Henle's loop it is useful as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, decreasing of intraocular pressure, acute or chronic bronchitis, in the treatment of cerebral edema caused by trauma, ischemia, concussion of the brain, metastases or epileptic attacks and in the treatment of nasal infections caused by allergens.

The ability of a substance to exist in more than one crystal form is defined as polymorphism and these different crystal forms are named "polymorph modifications" or "polymorphs". In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. Polymorphism is found in several organic compounds. Among medicaments polymorphism is found in about 70% of barbiturates, 60% of sulfonamides and 60% of steroids and about 50% of medicaments of the said classes are not present on the market in their most stable forms (T. Laird, Chemical Development and Scale-up in the Fine Chemical Industry, Principles and Practices, Course Manual, Scientific Update, Wyvern Cottage, 1996).

The different polymorphs of a substance possess different energies of the crystal lattice and, thus, in solid state they show different physical properties such as form, density, melting point, colour, stability, dissolution rate, milling facility, granulation, compacting, etc., which in medicaments may affect the possibility of the preparation of pharmaceutical forms, their stability, dissolution and bioavailability and, consequently, their action.

Polymorphism of medicaments is the object of studies of interdisciplinar expert teams [J. Haleblian, W. McCrone, *J. Pharm. Sci.* 58 (1969) 911; L. Borka, *Pharm. Acta Helv.* 66 (1991) 16; M. Kuhnert-Brandstätter, *Pharmazie* 51 (1996) 443; H. G. Brittain, *J. Pharm. Sci.* 86 (1997) 405; W. H. Streng, DDT 2 (1997) 415; K. Yoshii, *Chem. Pharm. Bull.* 45 (1997) 338, etc.] since a good knowledge of polymorphism represents a precondition for a critical observation of the whole process of medicament development. Thus, at deciding on the production of a pharmaceutical form in solid state and with regard to the dose size, stability, dissolution and anticipated action, it is necessary to determine the existence of all solid state forms (on the market some computer programmes can be found, e.g. >>Polymorph<< as a module of >>Cerius2<< programme, MSI Inc., USA) and to determine the stability, dissolution and thermodynamic properties of each of them. Only on the basis of these determinations the appropriate polymorph can be selected for the development of pharmaceutical formulations.

From the great number of such efforts only a few will be mentioned. Thus, Gordon et al. (U.S. Pat. No. 4,476,248) protected a new crystal form of ibuprofen and a process for the preparation thereof; Bunnell et al. (EP 733 635) protected a new crystal form, a process for preparation thereof and a pharmaceutical formation of the medicament olanzapine containing this new crystal form; R. B. Gandhi et al. (EP 749 969) protected a new process for the preparation of polymorph form I of stavudine from a mixture of one or more forms I, II and III; A. Caron et al. (EP 708 103) protected a new crystal form of irbesartane, a process for the preparation thereof and pharmaceutical formulations containing this crystal form.

It is known [*Acta Cryst.* B34 (1978), 2659–2662 and *Acta Cryst.* B34 (1978), 1304–1310] that torasemide can exist in two crystal modifications differing with regard to the parameters of a single cell, which is confirmed by X-ray diffraction on their monocrystals. Both modifications are formed simultaneously by the slow evaporation of the solvent from a solution of torasemide in a mixture petroleum ether/ethanol. The modification I with melting point 169° C. crystallizes monoclinically in the space group P $2_1$/c (prisms), while the modifications II with melting point 162° C. crystallizes monoclinically in the space group P 2/n (foils). Additionally, for the modification I the melting point 169.22° C. is stated in *Iyakuhin Kenkyu* 25 (1994), 734–750.

According to Example 71 of DE 25 16 025 torasemide in a crystal form with melting point 163–164° C. is obtained.

In U.S. Pat. No. 4,743,693 and U.S. reissue 34,580 or U.S. Pat. No. 4,822,807 and U.S. reissue 34,672 there is disclosed a process for the preparation of a stable modification I of torasemide from an unstable modification II of torasemide by adding a catalytic amount (1%) of a stable modification I of torasemide into a suspension of the unstable modification in water and stirring the mixture at a temperature from room temperature to 90° C. within 3 hours to 14 days. In U.S. Pat. No. 4,743,693 and U.S. reissue 34,580 it is stated that the stable modification I of torasemide (monoclinic, space group P$2_1$/c) has a melting point of 162° C. and the unstable modification II of torasemide (monoclinic, space group P 2/n) has a melting point 169° C., which is contrary to the statements in *Acta Cryst.* B34 (1978), 2659–2662, *Acta Cryst.* B34 (1978), 1304–1310 and *Iyakuhin Kenkyu* 25 (1994), 734–750.

In the abstract of U.S. Pat. No. 4,822,807 the authors ascribe the melting point 162° C. to the stable polymorph I of torasemide and the melting point 169° C. to the unstable polymorph II of torasemide, whereas in the claims of the said patent different melting points for either polymorph are stated, namely for polymorph I the melting point 169° C. and for polymorph II the melting point 162° C.

In the abstract of U.S. reissue 34,672 the authors ascribe the melting point 162° C. to the pure modifications I of torasemide and the melting point 169° C. to the modification II of torasemide, whereas in the claims the melting point 159–161.5° C. for the pure polymorph I and the melting point from about 157.5 to about 160° C. for the unstable polymorph II are stated.

SUMMARY OF INVENTION

It has now been surprisingly found that by a controlled acidifying of alkaline solutions of torasemide with inorganic or organic acids with or without addition of a seed crystal at a temperature between 0 and 35° C. within 15 minutes to 25 hours, a new crystal modification III of torasemide can be prepared.

By the alkaline solutions of torasemide according to the process of the present invention there are meant an alkaline extract of the original reaction mixture for the synthesis of torasemide, alkaline solutions of any crystal modification I, II or III of torasemide or alkaline solutions of any mutual mixtures of crystal modifications I, II or III of torasemide.

In the process of the present invention for the preparation of alkaline solutions of torasemide modifications, water solutions of lithium, sodium and potassium hydroxide as well as water solutions of sodium and potassium carbonate can be used.

The acidifying of the alkaline torasemide solutions according to the invention can be performed in inorganic acids such as hydrochloric, sulfuric, phosphoric and nitric acids and in organic acids such as formic, acetic, propionic, oxalic, tartaric, methanesulfonic and p-toluenesulfonic acids.

As the seed crystal in the processes of the present invention crystal powder of one of the isostructure substances, particularly crystal powder of the crystal modification III of torasemide can be used.

It has additionally been found that by using the process of the present invention no decomposition of torasemide occurs and the impurities that may be present in the alkaline extract of the original reaction mixture for the synthesis of torasemide or in modifications I, II or III of torasemide pass, by the present process, into bases, i.e. a chemically pure crystal modification III of torasemide is obtained.

Moreover, it has been found that the new crystal modification III of torasemide is stable under normal storage conditions as well as at being subjected to increased humidity, which means that it is neither transformed into the unstable modification II of torasemide nor into the stable modification I of torasemide.

The new crystal modification III of torasemide has a characteristic X-ray powder pattern obtained by X-ray diffraction on a powder sample of the new crystal modification III of torasemide in the instrument PHILIPS PW3710 under Cu X-rays [λ(CuKα$_1$)=1.54046 Å and λ(CuKα$_2$)=1.54439 Å]. Thus obtained characteristics spacings between lattice planes designated by >>d<< and expressed in Angström units and their corresponding characteristic relative intensities designated by >>I/I$_0$<< and expressed in % are represented in Table 1.

TABLE 1

| Modification III | |
|---|---|
| d (Å) | I/I$_0$ (%) |
| 15.3898 | 2.8 |
| 12.5973 | 5.4 |

TABLE 1-continued

| Modification III | |
|---|---|
| d (Å) | I/I$_0$ (%) |
| 11.4565 | 5.8 |
| 9.7973 | 69.8 |
| 9.5493 | 76.6 |
| 8.6802 | 28.5 |
| 8.2371 | 100.0 |
| 7.6351 | 10.2 |
| 7.3356 | 13.0 |
| 6.9759 | 1.2 |
| 6.5351 | 10.0 |
| 6.3240 | 7.9 |
| 6.1985 | 4.5 |
| 5.9521 | 0.6 |
| 5.6237 | 24.4 |
| 5.5623 | 29.7 |
| 5.4040 | 19.6 |
| 5.1119 | 10.3 |
| 4.8738 | 22.7 |
| 4.7865 | 46.9 |
| 4.6986 | 45.7 |
| 4.5985 | 17.9 |
| 4.4602 | 24.7 |
| 4.3405 | 90.0 |
| 4.2552 | 20.7 |
| 4.1829 | 19.9 |
| 4.0768 | 19.9 |
| 3.9377 | 47.1 |
| 3.8659 | 29.3 |
| 3.8429 | 35.3 |
| 3.7801 | 42.8 |
| 3.7248 | 11.9 |
| 3.6239 | 31.7 |
| 3.5556 | 20.5 |
| 3.4825 | 7.8 |
| 3.4130 | 8.1 |
| 3.3055 | 15.5 |
| 3.2298 | 8.2 |
| 3.1786 | 10.7 |
| 3.1278 | 5.6 |
| 3.0699 | 7.1 |
| 3.0078 | 17.5 |
| 2.9549 | 5.1 |
| 2.9056 | 4.3 |
| 2.8541 | 1.8 |
| 2.7686 | 13.9 |
| 2.6988 | 5.7 |
| 2.6610 | 6.3 |
| 2.6293 | 7.3 |
| 2.5549 | 3.7 |
| 2.5236 | 2.0 |
| 2.4485 | 5.3 |
| 2.4161 | 6.7 |
| 2.3671 | 2.0 |
| 2.3133 | 3.6 |
| 2.2788 | 7.6 |
| 2.2312 | 3.4 |
| 2.1852 | 6.2 |
| 2.1468 | 3.0 |
| 2.0957 | 4.7 |
| 2.0617 | 4.1 |
| 2.0273 | 3.3 |
| 1.9896 | 3.1 |
| 1.9688 | 4.1 |
| 1.9274 | 2.6 |
| 1.8853 | 2.7 |
| 1.7931 | 2.1 |
| 1.7449 | 1.0 |
| 1.7169 | 1.8 |
| 1.6512 | 1.0 |
| 1.6122 | 0.8 |
| 1.5601 | 0.8 |
| 1.5320 | 0.3 |
| 1.5057 | 0.5 |
| 1.4521 | 0.3 |
| 1.3773 | 0.6 |

In addition, by recording the monocrystal of the new crystal modification III of torasemide in four circle PHILIPS PW 1100/Stoe&Cie diffractometer under Mo X-rays [λ(MoKα)=0.71073 Å] there were obtained the basic crystallographic data for a single cell, which show in comparison with the literature data for crystal modifications I and II of torasemide [*Acta Cryst.* B34 (1978), 2659–2662 and *Acta Cryst.* B34 (1978), 1304–1310] that this is an absolutely new crystal modification III of torasemide.

The basic crystallographic data (diffraction on monocrystal) for modifications I, II and the new crystal modification III of torasemide are represented in Table 2.

TABLE 2

| Parameter | Crystal modification of torasemide | | |
|---|---|---|---|
|  | I | II | III |
| crystal composition | monoclinic | monoclinic | monoclinic |
| space group | P $2_1$/c | P 2/n | P $2_1$/c |
| a (Å) | 13.308 | 20.446 | 11.430 |
| b (Å) | 8.223 | 11.615 | 19.090 |
| c (Å) | 31.970 | 16.877 | 16.695 |
| β (°) | 107.01 | 108.90 | 93.903 |
| V (Å$^3$) | 3345.5 | 3791.9 | 3634.7 |
| Z | 4 × 2 | 4 × 2 | 4 × 2 |

The new crystal modification III of torasemide prepared according to the process of the present invention can be transformed by the use of common processes to the crystal modification I of torasemide, i.e. it can be used as a starting material for the preparation of known crystal modification I of torasemide.

The new crystal modification III of torasemide prepared according to the invention can be transformed to pharmaceutically acceptable salts of torasemide by the use of common processes.

The dissolution profile (USP 23) of the new crystal modification III of toresamide in water and in artificial intestinal juice in comparison to dissolution profiles of known crystal modifications I and II of toresamide, in the same fluids, shows a significant difference.

IDR (Intrinsic Dissolution Rate) of the new crystal modification III of torasemide in a model of artificial gastric juice exceeds 1 mg cm$^{-2}$min$^{-1}$, which indicates a potential good bioavailability.

The new crystal modification III of torasemide is prepared according to the process of the present invention in the form of a flowable crystal powder of a prismatic habitude, which exhibits flowability, i.e. it comes in a "free flow" form, wherein no static charge accumulation occurs.

The new crystal modification III of torasemide prepared according to the process of the present invention can be used as a suitable torasemide form as a diuretic as well as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, for decreasing intraocular pressure, acute or chronic bronchitis, in the treatment of cerebral edema caused by trauma, ischemia, concussion of the brain, metastases or epileptic attacks and in the treatment of nasal infections caused by allergens.

The present invention also relates to pharmaceutical forms such as tablets containing the new crystal modification III of torasemide as the active ingredient combined with one or more pharmaceutically acceptable additives such as sugar, starch, starch derivatives, cellulose, cellulose derivatives, mould release agents, and antiadhesive agents and possibly agents for flowability regulation. When using the new crystal modification III of torasemide for the preparation of pharmaceutical forms, also process steps taking place in water, e.g. granulation, can be used.

The starting materials for the process of present invention i.e the alkaline extract of the original reaction mixture for torasemide synthesis can be prepared according to DE 25 16 025, whereas the modifications I and II of torasemide can be prepared according to *Acta Cryst.* B34 (1978), 1304–1310.

SUMMARY DRAWINGS

BEST AND VARIOUS MODES FOR CARRYING OUT INVENTION

Figure 1:
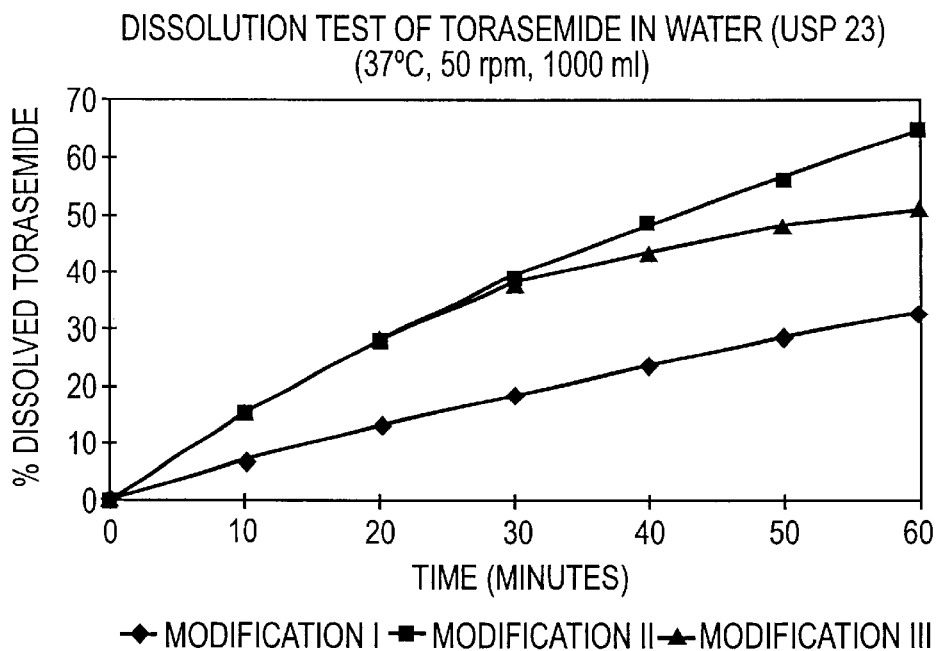
FIG. 1 is a graph of dissolution tests of torasemide in water.

The present invention is illustrated but in no way limited by the following Examples.

EXAMPLE 1

Technically pure new crystal modification III of torasemide:

The original alkaline extract of the reaction mixture for torasemide synthesis (1000 ml) prepared according to DE 25 16 025 was acidifed with 10% aqeuous acetic acid solution under the addition of 1.4 g of a crystal modification III of torasemide. The suspension was stirred at room temperature for 90 minutes. The crystals were sucked off, washed with 1 litre of demineralized water and dried in vacuum dryer at 50° C. for 3 hours. There were obtained 125 g of a crystal modification III of torasemide, m.p. 162–165° C.

The X-ray powder pattern of the thus obtained sample correspond to the new crystal modification III of torasemide. The content of torasemide according to the HPLCF method was >99%.

EXAMPLE 2

The crystal modification III of torasemide (1000 g) prepared according to the Example 1 was dissolved in a 10-fold amount of 5% aqueous potassium hydroxide solution and at the temperature of 20° C. the obtained solution was acidified with 5% aqueous hydrochloric acid solution under the addition of 10 g of a crystal modification III of torasemide. The suspension was stirred at 20° C. for 120 minutes. The crystal were sucked off, washed with 4 litres of demineralized water and dried in a vacuum dryer at 50° C. for 3 hours. There were obtained 961 g of a modification III of torasemide, m.p. 165° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 3

The crystal modification I of torasemide (1.00 g) prepared according to *Acta Cryst.* B34 (1978), 1304–1310 was dissolved in a 10-fold amount of 10% aqueous sodium carbonate solution and at the temperature of 15° C. the obtained solution was acidified with 5% aqueous sulfuric acid solution under the addition of 0.10 g of the modification III of torasemide. The suspension was stirred at 15° C. for 120 minutes. The crystals were sucked off, washed with 4 ml of demineralized water and dried in a vacuum dryer at 50° C. for 3 hours. There were obtained 0.95 g of a crystal modification III of torasemide, m.p. 165–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 4

The crystal modification II of torasemide (1.00 g) prepared according to *Acta Cryst.* B34 (1978), 1304–1310 was dissolved in a 10-fold amount of 10% aqueous potassium carbonate solution and then at the temperature of 15° C. the obtained solution was acidified with 5% aqueous nitric acid solution under the addition of 0.10 g of a modification III of torasemide. The suspension was stirred at 15° C. for 120 minutes. The crystals were sucked off, washed with 4 ml of demineralized water and dried in a vacuum dryer at 50° C. for 3 hours. There were obtained 0.96 g of a crystal modification III of torasemide, m.p. 164–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 5

A mixture of crystal modifications I and II of torasemide (1.00 g) prepared according to *Acta Cryst.* B34 (1978), 1304–1310 was dissolved in a 10-fold amount of 10% aqueous lithium hydroxide solution and then at room temperature the obtained solution was acidified with 5% aqueous phosphoric acid solution under the addition of 0.10 g of a modification III of torasemide. The suspension was stirred at 15° C. for 240 minutes. The crystals were sucked off, washed with 4 ml of demineralized water and dried in a vacuum dryer at 50° C. for 3 hours. There were obtained 0.97 g of a crystal modification III of torasemide, m.p. 165–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 6

A mixture of crystal modifications I and III of torasemide (1.00 g) prepared according to *Acta Cryst.* B34 (1978), 1304–1310 and Example 1 was dissolved in a 10-fold amount of 5% aqueous potassium hydroxide solution and then at the temperature of 30° C. the obtained solution was acidified with 10% aqueous tartaric acid solution under the addition of 0.10 g of a modification III of torasemide. The suspension was stirred at 30° C. for 180 minutes. The crystals were sucked off, washed with 4 ml of demineralized water and dried in a vacuum dryer at 50° C. for 3 hours. There were obtained 0.93 g of a crystal modification III of torasemide, m.p. 164–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 7

A mixture of crystal modifications II and III of torasemide (1.00 g) prepared according to *Acta Cryst.* B34 (1978), 1304–1310 and Example 1 was dissolved in a 10-fold amount of 5% aqueous sodium hydroxide solution and then at the temperature of 35° C. the obtained solution was acidified with 5% aqueous propionic acid solution under the addition of 0.10 g of a modification III of torasemide. The suspension was stirred at 35° C. for 90 minutes. The crystals were sucked off, washed with 4 ml of demineralized water and dried in a vacuum dryer at 50° C. for 3 hours. There were obtained 0.87 g of a crystal modification III of torasemide, m.p. 165° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 8

A mixture of crystal modifications I, II and III of torasemide (1.00 g) prepared according to *Acta Cryst.* B34 (1978), 1304–1310 and Example 1 was dissolved in a 10-fold amount of 10% aqueous sodium carbonate solution and then at the temperature of 25° C. the obtained solution was acidified with 5% aqueous p-toluenesulfonic acid solution under the addition of 0.10 g of a modification III of torasemide. The suspension was stirred at 25° C. for 60 minutes. The crystals were sucked off, washed with 4 ml of demineralized water and dried in a vacuum dryer at 50° C. for 3 hours. There were obtained 0.93 g of a crystal modification III of torasemide, m.p. 164–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 9

A crystal modification I of torasemide (1.00 g) prepared according to *Acta Cryst.* B34 (1978), 1304–1310 was dissolved in a 10-fold amount of 10% aqueous potassium carbonate solution and then at the temperature of 15° C. the obtained solution was stepwise acidified with 10% aqueous acetic acid solution under the simultaneous stepwise lowering of the temperature of the mixture to 0° C. At this temperature the suspension was stirred for 25 minutes. The crystals were sucked off, washed with 4 ml of demineralized water and dried in a vacuum dryer at 50° C. for 3 hours. There were obtained 0.94 g of a crystal modification III of torasemide, m.p. 164–166° C.

The X-ray powder pattern of the thus obtained sample corresponded to the crystal modification III of torasemide. The content of torasemide according to the HPLC method was >99.5%, i.e. it corresponded to chemically pure torasemide.

EXAMPLE 10

Production of 2.5 mg tablets:

Torasemide of the crystal modification III was mixed with lactose and corn starch in a common manner, granulated with water, dried and sieved (granulate 1). Colloidal silicon dioxide and magnesium stearate were mixed, sieved and admixed into granulate 1. This mixture was then tabletized in a common manner. For the production of 100 000 tablets the following is required:

| | |
|---|---|
| torasemide-crystal modification III | 0.25 kg |
| lactose (Lactose Extra Fine Crystal HMS ®) | 6.05 kg |
| corn starch (Starch ®) | 1.60 kg |
| colloidal silicon dioxide (Aerosil 200 ®) | 60.00 g |
| magnesium stearate | 40.00 g |
| redistilled water | 1.20 kg |

EXAMPLE 11

Production of 100 mg tablets:

Torasemide of crystal modification III was mixed with lactose and corn starch and a part of magnesium stearate in a common manner. The mixture was compressed and sieved to obtain the desired grain size and distribution of grain size (granulate 1). Collodial silicon dioxide and magnesium stearate were mixed, sieved and admixed into granulate 1. This mixture was then tabletized in a common manner. For the production of 100 000 tablets the following is required:

| | |
|---|---|
| torasemide-crystal modification III | 10.0 kg |
| lactose (Lactose Extra Fine Crystal HMS ® | 2.0 kg |
| corn starch (Starch ®) | 7.7 kg |
| colloidal silicon dioxide (Aerosil 200 ®) | 0.2 kg |
| magnesium stearate | 0.1 kg |

EXAMPLE 12

The microcrystallinic modifications I, II and III of torasemide prepared according to *Acta Crst.* B34 (1978), 1304–1310 and Example 1 were subjected to dissolution testing in water, and in artificial intestinal juice, at 37° C. (USP 23), and results are reported in tables 3 and 4.

TABLE 3

Dissolution test of torasemide in water (USP 23) (37° C., 50 rpm., 1000 ml)

| | % Dissolved torasemide | | |
|---|---|---|---|
| Minutes | Mod. I | Mod. II | Mod. III |
| 0 | 0 | 0 | 0 |
| 10 | 6.7 | 15.1 | 15.6 |
| 20 | 13.0 | 27.8 | 28.1 |
| 30 | 18.5 | 39.2 | 37.7 |
| 40 | 23.5 | 48.8 | 43.6 |
| 50 | 28.5 | 56.3 | 48.5 |
| 60 | 32.8 | 65.1 | 51.1 |

TABLE 4

Dissolution test of torasemide in artificial intestinal juice (USP 23) (37° C., 50 rpm, pH 7.5, 1000 ml)

| | % Dissolved torasemide | | |
|---|---|---|---|
| Minutes | Mod. I | Mod. II | Mod. III |
| 0 | 0 | 0 | 0 |
| 10 | 29.4 | 73.3 | 41.0 |
| 20 | 40.5 | 92.6 | 59.8 |
| 30 | 48.4 | 95.5 | 70.2 |
| 40 | 54.2 | 96.8 | 77.6 |

TABLE 4-continued

Dissolution test of torasemide in artificial intestinal juice (USP 23) (37° C., 50 rpm, pH 7.5, 1000 ml)

| | % Dissolved torasemide | | |
|---|---|---|---|
| Minutes | Mod. I | Mod. II | Mod. III |
| 50 | 59.2 | 96.3 | 82.5 |
| 60 | 65.0 | 98.2 | 88.7 |

Figure 2:
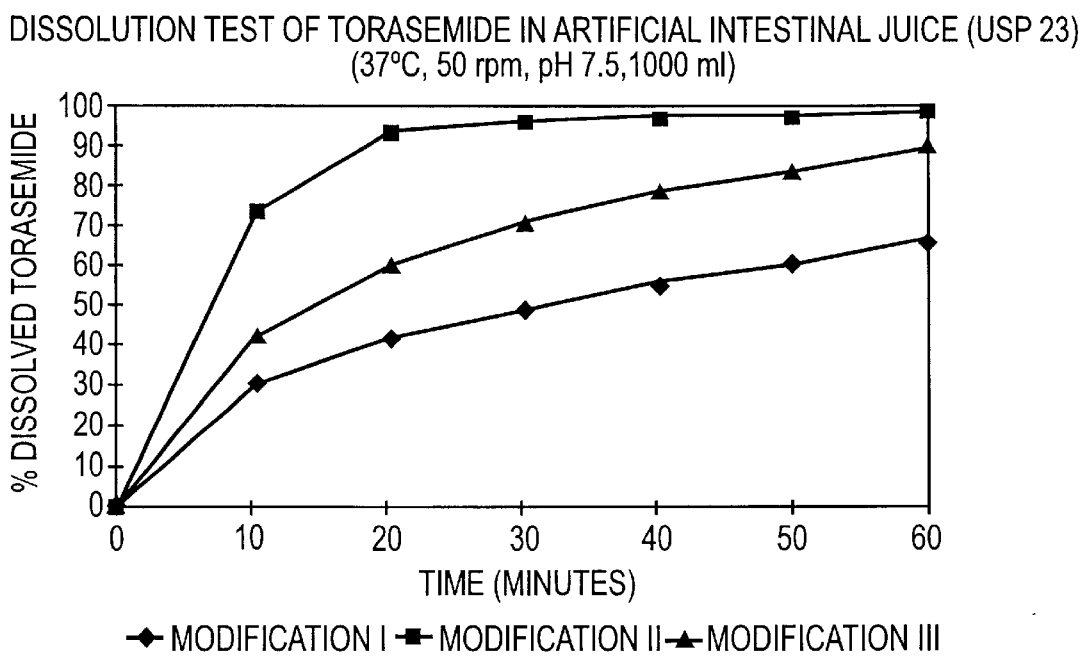
FIG. 2 is a graph of dissolution tests of torasemide in artificial intestinal juice.

The results reported in Table 3 were plotted in the FIG. 1. The results reported in Table 4 were plotted in the FIG. 2.

What is claimed is:

1. Crystal modification III of torasemide, wherein the characteristic X-ray powder pattern of its sample is represented by the following spacings between lattice planes;

| Crystal modification III of torasemide d(Å) |
|---|
| 15.3898 |
| 12.5973 |
| 11.4565 |
| 9.7973 |
| 9.5493 |
| 8.6802 |
| 8.2371 |
| 7.6351 |
| 7.3356 |
| 6.9759 |
| 6.5351 |
| 6.3240 |
| 6.1985 |
| 5.9521 |
| 5.6237 |
| 5.5623 |
| 5.4040 |
| 5.1119 |
| 4.8738 |
| 4.7865 |
| 4.6986 |
| 4.5985 |
| 4.4602 |
| 4.3405 |
| 4.2552 |
| 4.1829 |
| 4.0768 |
| 3.9377 |
| 3.8659 |
| 3.8429 |
| 3.7801 |
| 3.7248 |
| 3.6239 |
| 3.5556 |
| 3.4825 |
| 3.4130 |
| 3.3055 |
| 3.2298 |
| 3.1786 |
| 3.1278 |
| 3.0699 |
| 3.0078 |
| 2.9549 |
| 2.9056 |
| 2.8541 |
| 2.7686 |
| 2.6988 |
| 2.6610 |
| 2.6293 |
| 2.5549 |
| 2.5236 |
| 2.4485 |
| 2.4161 |
| 2.3671 |
| 2.3133 |
| 2.2788 |

-continued

| Crystal modification III of torasemide d(Å) |
|---|
| 2.2312 |
| 2.1852 |
| 2.1468 |
| 2.0957 |
| 2.0617 |
| 2.0273 |
| 1.9896 |
| 1.9688 |
| 1.9274 |
| 1.8853 |
| 1.7931 |
| 1.7449 |
| 1.7169 |
| 1.6512 |
| 1.6122 |
| 1.5601 |
| 1.5320 |
| 1.5057 |
| 1.4521 |
| 1.3773 |

2. Crystal modification III of torasemide according to claim 1, having the following crystallographic characteristics:

| Parameter | Crystal modification III torasemide |
|---|---|
| crystal composition | monoclinic |
| spacegroup | P $2_1$/c |
| a (Å) | 11.430 |
| b (Å) | 19.090 |
| c (Å) | 16.695 |
| β (°) | 93.903 |
| V (Å$^3$) | 3634.7 |
| Z | 4 × 2 |

3. Crystal modification III of torasemide according to claim 1, which is chemically pure.

4. Crystal modification III of torasemide according to claim 1, which does not contain water.

5. Crystal modification III of torasemide according to claim 1, which does not contain a solvent.

6. A process for the preparation of crystal modification III of torasemide according to claim 1, wherein an alkaline torasemide solution is subjected to controlled acidifying with an inorganic or organic acid at a temperature between 0° C. to 35° C. for 15 minutes to 25 hours.

7. The process for the preparation of crystal modification III of torasemide according to claim 6, wherein the alkaline torasemide solution is an alkaline extract of the original reaction mixture for the synthesis of torasemide.

8. The process for the preparation of crystal modification III of torasemide according to claim 6, wherein the alkaline torasemide solution is an alkaline solution of any crystal modification I, II, or III of torasemide or an alkaline solution of any mutual mixture of crystal modifications I, II, or III of torasemide.

9. The process according to claim 6, wherein a water solution of lithium, sodium, or potassium hydroxide or a water solution of sodium of potassium carbonate is used for the preparation of the alkaline torasemide solution.

10. The process according to claim 6, wherein an inorganic acid or an organic acid is used for acidifying.

11. Process according to claim 6, wherein crystal powder of one of the isocrystallinic substances of torasemide is used as the seed crystal.

12. A starting material for the preparation of crystal modification I of torasemide comprising crystal modification III of torasemide according to claim 1.

13. A starting material for the preparation of pharmaceutically acceptable salts of torasemide comprising crystal modification III of torasemide according to claim 1.

14. A pharmaceutical composition for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, for decreasing intraocular pressure, acute or chronic bronchitis, in the treatment of cerebral edema caused by trauma, ischemia, concussion of the brain, metastases or epileptic attacks, and in the treatment of nasal infections caused by allergens comprising a diuretically effective amount of crystal modification III of torasemide according to claim 1.

15. A pharmaceutical composition, which contains as the active ingredient the crystal modification III of torasemide according to claim 1 combined with one or more pharmaceutically acceptable carriers, additives, or diluents.

16. The pharmaceutical composition according to claim 15, wherein the composition is a tablet.

17. The process according to claim 6, wherein the inorganic acid is selected from the group consisting of hydrochloric, sulfuric, phosphoric, and nitric acid.

18. The process according to claim 6, wherein the organic acid is formic, acetic, propionic, oxalic, tartaric, methanesulfonic, or p-toluensulfonic acid.

19. The process according to claim 6, wherein a seed crystal is added in the controlled acidifying.

20. The process according to claim 11, wherein the seed crystal is crystal powder of crystal modification III of torasemide.

21. The process according to claim 6, wherein no seed crystal is added in the controlled acidifying.

22. A method for preventing heart or heart tissue damages caused by metabolic or ionic abnormalities associated with ischemia, for decreasing intraocular pressure, and for the treatment of thrombosis, angina pectoris, asthma, hypertension, nephroedema, pulmonary edema, primary and secondary aldosteronism, Bartter's syndrome, tumours, glaucoma, acute or chronic bronchitis, cerebral edema caused by trauma, ischemia, concussion of the brain, metastases or epileptic attacks, and nasal infections caused by allergens comprising administering a diuretically effective amount of crystal modification III of torasemide according to claim 1 to a patient in need thereof.

23. A pharmaceutical composition, which comprises a diuretically effective amount of crystal modification III of torasemide or a pharmaceutically acceptable salt thereof according to claim 1 and a pharmaceutically acceptable carrier.

24. A method of producing diuresis, which comprises administering a diuretically effective amount of the composition of claim 23 to a patient in need thereof.

* * * * *